(12) United States Patent
Moriya

(10) Patent No.: US 9,107,855 B2
(45) Date of Patent: Aug. 18, 2015

(54) ORGANOPOLYSILOXANE, COSMETIC CONTAINING THEREOF, AND METHOD FOR PREPARING ORGANOPOLYSILOXANE

(71) Applicant: SHIN-ETSU CHEMICAL CO., LTD., Tokyo (JP)

(72) Inventor: Hiroyuki Moriya, Annaka (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 161 days.

(21) Appl. No.: 13/800,674

(22) Filed: Mar. 13, 2013

(65) Prior Publication Data

US 2013/0253215 A1    Sep. 26, 2013

(30) Foreign Application Priority Data

Mar. 22, 2012    (JP) ................. 2012-065762

(51) Int. Cl.

| | | |
|---|---|---|
| *C07F 7/18* | (2006.01) | |
| *A61K 8/894* | (2006.01) | |
| *A61Q 1/12* | (2006.01) | |
| *A61K 8/02* | (2006.01) | |
| *C08G 77/14* | (2006.01) | |
| *C08G 77/46* | (2006.01) | |
| *C08L 83/04* | (2006.01) | |
| *A61Q 1/08* | (2006.01) | |
| *A61Q 1/10* | (2006.01) | |
| *A61Q 19/00* | (2006.01) | |
| *C08G 77/12* | (2006.01) | |

(52) U.S. Cl.

CPC .............. *A61K 8/894* (2013.01); *A61K 8/022* (2013.01); *A61Q 1/12* (2013.01); *C08G 77/14* (2013.01); *C08G 77/46* (2013.01); *C08L 83/04* (2013.01); *A61Q 1/08* (2013.01); *A61Q 1/10* (2013.01); *A61Q 19/00* (2013.01); *C08G 77/12* (2013.01)

(58) Field of Classification Search

USPC .......................................... 556/445, 446, 449
See application file for complete search history.

(56) References Cited

U.S. PATENT DOCUMENTS

| | | | |
|---|---|---|---|
| 2003/0044371 | A1 | 3/2003 | Walele et al. |
| 2007/0202069 | A1 | 8/2007 | Tamareselvy et al. |
| 2007/0203311 | A1 | 8/2007 | Roy et al. |
| 2010/0004201 | A1 | 1/2010 | Matsuo et al. |
| 2010/0036062 | A1 | 2/2010 | Okawa |
| 2011/0098420 | A1 | 4/2011 | Takizawa et al. |
| 2011/0248314 | A1 | 10/2011 | Takei et al. |
| 2012/0269747 | A1 | 10/2012 | Iimura et al. |

FOREIGN PATENT DOCUMENTS

| | | |
|---|---|---|
| CN | 101106970 A | 1/2008 |
| CN | 101389694 A | 3/2009 |
| CN | 101404978 A | 4/2009 |
| CN | 101472979 A | 7/2009 |
| EP | 1847262 A1 | 10/2007 |
| JP | A-7-025987 | 1/1995 |
| JP | A-2002-327126 | 11/2002 |
| JP | A-2009-256670 | 11/2009 |
| JP | A-2010-163602 | 7/2010 |
| JP | B2-4766222 | 9/2011 |
| WO | WO2009/025924 A2 * | 2/2009 |
| WO | WO 2011/049246 A1 | 4/2011 |

OTHER PUBLICATIONS

Apr. 4, 2014 Search Report issued in European Patent Application No. 13001377.4.
Feb. 13, 2015 Search Report issued in Chinese Application No. 2013100948993.

* cited by examiner

*Primary Examiner* — Sudhakar Katakam
*Assistant Examiner* — Pancham Bakshi
(74) *Attorney, Agent, or Firm* — Oliff PLC

(57) ABSTRACT

The present invention is an organopolysiloxane shown by the following average composition formula (1),

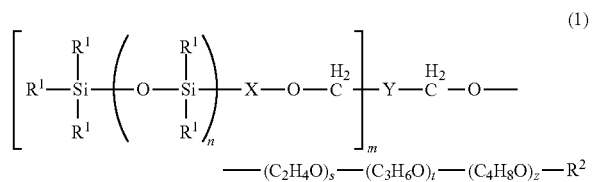

wherein each of $R^1$ independently represents a monovalent hydrocarbon group having 1 to 12 carbon atoms; $R^2$ represents any of a hydrogen atom, a monovalent hydrocarbon group having 1 to 15 carbon atoms, and a monovalent acyl group having 1 to 6 carbon atoms; "n" represents an integer of 0 to 1000; "m" represents 2 or 3; "X" represents a divalent hydrocarbon group having 2 to 15 carbon atoms; Y represents $C-CH_2-CH_3$ when "m" represents 2, while representing a carbon atom when "m" represents 3; "s" represents an integer of 0 to 100; "t" represents an integer of 0 to 50; and "z" represents an integer of 0 to 50. Organopolysiloxane gives a cosmetic with excellent emulsion stability, temporal stability, and cosmetic durability, and excellent dispersion properties to powders.

4 Claims, No Drawings

ORGANOPOLYSILOXANE, COSMETIC CONTAINING THEREOF, AND METHOD FOR PREPARING ORGANOPOLYSILOXANE

This application claims priority to Japanese Application No. 2012-065762, filed in Japan on Mar. 22, 2012.

BACKGROUND OF THE INVENTION

1. Field of the Invention

The present invention relates to a novel organopolysiloxane, a cosmetic which contains this, and a method for preparing an organopolysiloxane.

2. Description of the Related Art

In general, a secreted substance of human such as a sweat, a tear, and a sebum causes cosmetic deterioration. Especially in a make-up cosmetic, a sebum which is secreted from a skin is mixed with an oil in a cosmetic thereby excessively moistening powders in the cosmetic so that this becomes a major factor to cause cosmetic deterioration. Accordingly, in order to reduce amount of an oil in the cosmetic which is remained on a skin, a volatile oil material such as decamethyl cylcopentasiloxane has been studied as a part of the oil to be blended.

In addition, friction, water, and so forth are external factors for deterioration of cosmetic durability. Accordingly, to remedy the deterioration of cosmetic durability due to a water-soluble substance such as a sweat and a tear, or to avoid the loss of a water-soluble substance, a sedum, and so on in a skin thereby prolonging a skin protection effect, practically a silicone oil is added to enhance water-repellency. In a water-in-oil emulsion composition, to obtain freshness and good water-repellency with less stickiness, a silicone oil is used as the oil; but, in the water-in-oil emulsion which contains this silicone oil, it has been difficult to obtain an emulsion having good stability if a conventionally used emulsifier such as a polyoxyalkylene fatty acid ester is used.

Accordingly, methods wherein a polyoxyalkylene-modified organopolysiloxane (polyether-modified silicone) which has good compatibility with the silicone oil in the aforementioned water-in-oil emulsion is used have been proposed (Patent Documents 1 to 6). However, in the emulsion compositions like this, there still remains problems to obtain excellent emulsion stability and temporal stability; especially when this composition is used in a cosmetic, a surfactant which can secure excellent emulsion stability and temporal stability to a silicone oil and other oil materials used in a general cosmetic while keeping characteristics of these oil materials has been wanted. In addition, in the case that powders are included in a cosmetic, it is required that there will be no change such as agglomeration of powders and that the powders have excellent dispersion stability. Alternatively, a polyether-modified silicone which has a dendrimer-like branched silicone structure has been known; but structure of the dendrimer silicone part is so unique that a complicated process is necessary in its preparing process; and thus, there have been problems that not only its production cost is high but also production of a single product thereof is difficult (Patent Document 6).

CITATION LIST

Patent Literature

[Patent Document 1] Japanese Patent Laid-Open Publication No. H07-25987,
[Patent Document 2] Japanese Patent Laid-Open Publication No. 2002-327126
[Patent Document 3] Japanese Patent Laid-Open Publication No. 2009-256670
[Patent Document 4] Japanese Patent Laid-Open Publication No. 2010-163602
[Patent Document 5] Japanese Patent No. 4766222
[Patent Document 6] WO2011/049246

SUMMARY OF THE INVENTION

The present invention was made in view of the above situation and thus has an object to provide an organopolysiloxane which can give a cosmetic which has excellent emulsion stability, temporal stability, and cosmetic durability, and in addition, an organopolysiloxane which has excellent dispersion properties to powders.

To solve the problems mentioned above, according to the present invention, an organopolysiloxane which is shown by the following average composition formula (1) is provided,

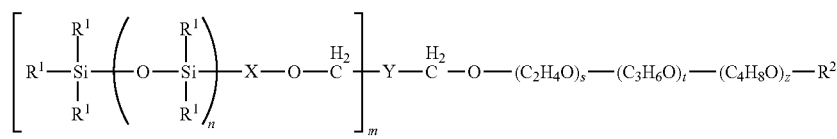

(1)

wherein each of $R^1$ independently represents a monovalent hydrocarbon group having 1 to 12 carbon atoms; $R^2$ represents any of a hydrogen atom, a monovalent hydrocarbon group having 1 to 15 carbon atoms, and a monovalent acyl group having 1 to 6 carbon atoms; "n" represents an integer of 0 to 1000; "m" represents 2 or 3; "X" represents a divalent hydrocarbon group having 2 to 15 carbon atoms; Y represents the below-shown formula when "m" represents 2, while representing a carbon atom when "m" represents 3; "s" represents an integer of 0 to 100; "t" represents an integer of 0 to 50; and "z" represents an integer of 0 to 50.

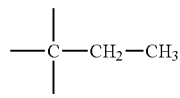

The organopolysiloxane which has the specific structure as mentioned above is characterized by that it has 2 to 3 polysiloxane chains per one molecule, wherein these chains are hydrophobic groups which are branched from one hydrophilic group via a specific spacer, so that the polysiloxane chains are widely spreading; and thus, a cosmetic which contains this can have excellent emulsion stability and temporal stability with excellent cosmetic durability. In addition, this organopolysiloxane has excellent dispersion stability to powders.

In addition, the present invention provides a cosmetic wherein the afore-mentioned organopolysiloxane is contained therein.

A cosmetic of the present invention has excellent emulsion stability, temporal stability, and cosmetic durability. In addition, a cosmetic comprised of the organopolysiloxane of the present invention, powders, and a silicone oil has excellent dispersion stability.

Further, the present invention provides a method for preparing of an organopolysiloxane wherein a compound shown by the following average composition formula (2) and a compound shown by the following general formula (3) are reacted in the presence of a transition metal catalyst, The organopolysiloxane of the present invention can give a cosmetic which has excellent emulsion stability, temporal stability, and cosmetic durability. In addition, this organopolysiloxane is excellent in dispersion properties to powders.

DESCRIPTION OF THE EMBODIMENTS

Hereinafter, the present invention will be explained in more detail.

Novel Organopolysiloxane

According to the present invention, an oragnopolysiloxane shown by the following average composition formula (1) is provided,

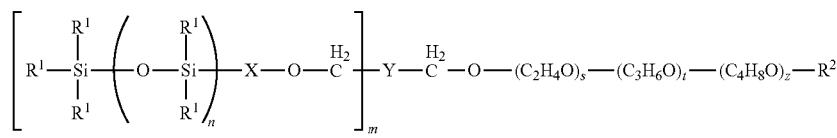

(1)

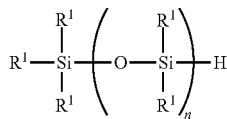

(2)

wherein each of $R^1$ independently represents a monovalent hydrocarbon group having 1 to 12 carbon atoms, and "n" represents an integer of 0 to 1000, $$\left[X'\!\!-\!\!O\!\!-\!\!\overset{H_2}{C}\right]_m\!\!-\!\!Y\!\!-\!\!\overset{H_2}{C}\!\!-\!\!O\!\!-\!\!(C_2H_4O)_s\!\!-\!\!(C_3H_6O)_t\!\!-\!\!(C_4H_8O)_z\!\!-\!\!R^2$$

(3)

wherein X' represents a divalent hydrocarbon group having a C—C double bond at a terminal and has 2 to 15 carbon atoms; "m" represents 2 or 3; Y represents the below-shown formula when "m" represents 2, while representing a carbon atom when "m" represents 3; $R^2$ represents any of a hydrogen atom, a monovalent hydrocarbon group having 1 to 15 carbon atoms, and a monovalent acyl group having 1 to 6 carbon atoms; "s" represents an integer of 0 to 100; "t" represents an integer of 0 to 50; and "z" represents an integer of 0 to 50.

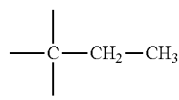

According to the method like this for preparing of an organopolysiloxane, the organopolysiloxane which is shown by the formula (1) can be manufactured efficiently.

Further, the afore-mentioned transition metal catalyst contains preferably at least one element of platinum and rhodium.

The transition metal catalyst like this is preferable because the reaction between the compound shown by the average composition formula (2) and the compound shown by the general formula (3) may take place sufficiently well.

wherein each of $R^1$ independently represents a monovalent hydrocarbon group having 1 to 12 carbon atoms; $R^2$ represents any of a hydrogen atom, a monovalent hydrocarbon group having 1 to 15 carbon atoms, and a monovalent acyl group having 1 to 6 carbon atoms; "n" represents an integer of 0 to 1000; "m" represents 2 or 3; "X" represents a divalent hydrocarbon group having 2 to 15 carbon atoms; Y represents the below-shown formula when "m" represents 2, while representing a carbon atom when "m" represents 3; "s" represents an integer of 0 to 100; "t" represents an integer of 0 to 50; and "z" represents an integer of 0 to 50.

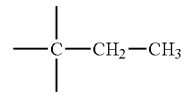

In the general formula (1), each of $R^1$ independently represents a monovalent hydrocarbon group having 1 to 12 carbon atoms. Illustrative example of $R^1$ includes an alkyl group such as a methyl group, an ethyl group, a propyl group, a butyl group, a pentyl group, a hexyl group, a heptyl group, an octyl group, a nonyl group, and a decyl group; a cycloalkyl group such as a cyclopentyl group and a cyclohexyl group; and a phenyl group, a tolyl group, a benzyl group, and a phenethyl group. Preferable examples thereof are a methyl group, a butyl group, and a phenyl group. In addition, preferably 50% or more of $R^1$ is a methyl group, or still more preferably 70% or more of $R^1$ is a methyl group.

$R^2$ represents any of a hydrogen atom, a monovalent hydrocarbon group having 1 to 15 carbon atoms, and a monovalent acyl group having 1 to 6 carbon atoms. Illustrative example of $R^2$ includes a hydrogen atom, and an alkyl group such as a methyl group, an ethyl group, a propyl group, a butyl group, a pentyl group, and a hexyl group; a phenyl group; and an acyl group such as an acetyl group, a propionyl group, and a benzoyl group.

"X" represents a divalent hydrocarbon group having 2 to 15 carbon atoms; and illustrative example thereof includes —(CH$_2$)$_2$—, —(CH$_2$)$_3$—, —(CH$_2$)$_4$—, —CH$_2$CH(CH$_3$)

$CH_2$—, —$(CH_2)_8$—, and —$(CH_2)_{11}$—, while —$(CH_2)_2$—, —$(CH_2)_3$—, and —$CH_2CH(CH_3)CH_2$— are preferable.

Y represents a carbon atom or the below-shown formula, wherein

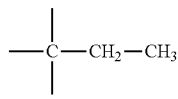

Y represents the below-shown formula when "m" is 2, while representing a carbon atom when "m" is 3.

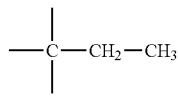

"n" represents an integer of 0 to 1000, or preferably 0 to 100. "m" represents preferably 2, or 3. "s" represents an integer of 0 to 100, preferably 1 to 80, or more preferably 2 to 50. "t" represents an integer of 0 to 50, or preferably 0 to 30. "z" represents an integer of 0 to 50, or preferably 0 to 20. Further, s+t+z is 0 to 200, preferably 1 to 100, or more preferably 2 to 50.

In addition, these alkylene ether portions are a random or a block copolymer.

Preparing of an Organopolysiloxane

The method of the present invention is to react an organopolysiloxane shown by the following average composition formula (2) with a compound shown by the following general formula (3) in the presence of a transition metal catalyst,

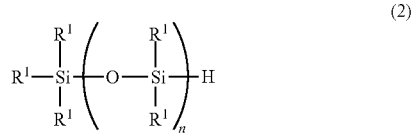

wherein each of $R^1$ independently represents a monovalent hydrocarbon group having 1 to 12 carbon atoms, and "n" represents an integer of 0 to 1000,

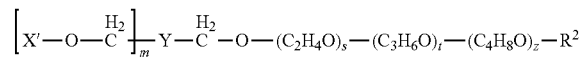

wherein X' represents a divalent hydrocarbon group having a C—C double bond at a terminal and has 2 to 15 carbon atoms; "m" represents 2 or 3; Y represents the below-shown formula when "m" represents 2, while representing a carbon atom when "m" represents 3; $R^2$ represents any of a hydrogen atom, a monovalent hydrocarbon group having 1 to 15 carbon atoms, and a monovalent acyl group having 1 to 6 carbon atoms; "s" represents an integer of 0 to 100; "t" represents an integer of 0 to 50; and "z" represents an integer of 0 to 50.

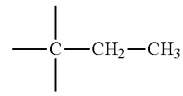

the general formula (3), X' represents a divalent hydrocarbon group having a C—C double bond at a terminal and has 2 to 15 carbon atoms; and illustrative example thereof includes CH—CH—, $CH_\_CH$—$CH_2$—, $CH_\_CH$—$(CH_2)_2$—, CH═C($CH_3$)$CH_2$—, CH═CH— $(CH_2)_6$—, and CH═CH—$(CH_2)_9$—, while preferable examples thereof are CH═CH—$CH_2$— and CH═C($CH_3$)$CH_2$—.

Y, $R^2$, "n", "m", "s", "t", and "z" represent the same meanings as before.

A compound shown by the general formula (3) is manufactured preferably by the method wherein raw materials of trimethylolpropane diallyl ether or pentaerythritol triallyl ether are subjected to an addition reaction with ethylene oxide, propylene oxide, and butylene oxide, solely or simultaneously, in the presence of a base catalyst or an acid catalyst. The addition reaction of the foregoing alkylene oxides to a hydroxyl group is a technology in the public domain. Purities of trimethylolpropane diallyl ether and pentaerythritol triallyl ether are preferably 50% or higher, or more preferably 70% or higher.

A platinum catalyst or a rhodium catalyst may be used as the transition metal catalyst. Preferably, chloroplatinic acid, alcohol-modified chloroplatinic acid, and chloroplatinic acid-divinyl siloxane complex are used. As to the use amount thereof, a catalytically effective amount is used; and thus, amount thereof is usually 0.1 to 100 ppm, preferably 0.5 to 50 ppm, or more preferably 1 to 20 ppm, as the amount of platinum or rhodium.

Reaction temperature is not particularly restricted. When an organic solvent is used, the temperature thereof is not higher than its boiling point; and when solvent is not used, the temperature thereof is preferably in the range of 50 to 140° C. If the temperature is 140° C. or lower, there is no fear of internal migration of the terminal C—C double bond; and in addition, more efficient reactivity can be expressed. Reaction time is not particularly restricted either, though preferably 1 to 10 hours.

The reaction may be carried out in an organic solvent as necessary. Illustrative example of the organic solvent includes an aromatic hydrocarbon such as toluene and xylene; a lower alcohol such as ethanol and isopropyl alcohol; an aliphatic or an alicyclic hydrocarbon such as n-pentane, n-hexane, and cyclohexane; a halogenated hydrocarbon such as dichloromethane, chloroform, and carbon tetrachloride; and an ether such as tetrahydrofuran and dioxane. Preferably, an aromatic, an aliphatic or an alicyclic hydrocarbon, or a lower alcohol is used.

Equivalent ratio for the reaction of the compound shown by the general formula (3) to the organopolysiloxane shown by the general formula (2) is preferably 0.7 to 1.3 equivalents, or more preferably 0.9 to 1.1 equivalents, relative to 1 equivalent of the organopolysiloxane.

The polyoxyalkylene-containing organopolysiloxane of the present invention may be used in a personal care composition, a cosmetic, a fiber treatment, a coating material, a resin property modifier, and the like.

Cosmetic

Cosmetic of the present invention may contain the organopolysiloxane of the present invention, especially the polyoxyalkylene-containing organopolysiloxane prepared by the foregoing method, as it is.

Into the cosmetic of the present invention may be added, in addition to the foregoing organopolysiloxane, substances which are used in a usual cosmetic; and thus, illustrative example thereof includes a solid, a semi-solid or liquid state oils, water, alcohols, a water-soluble polymer, a film-forming material, a surfactant, an oil-soluble gelation agent, an organic-modified clay mineral, a resin, powders, a UV-absorber, a moisturizer, an antibacterial preservative, an antibacterial agent, a fragrance, salts, an antioxidant, a pH controller, a chelating agent, an algefacient, an anti-inflammatory agent, a skin care ingredient, vitamins, an amino acid, a nucleic acid, a hormone, and a clathrate compound. Hereinafter, illustrative examples of these substances will be mentioned, though the present invention is not restricted by them.

As to the oils usable in the present invention, following substances may be mentioned. Meanwhile, POE means polyoxyethylene. Illustrative example of the natural vegetable and animal fatty oil and the semi-synthetic oil includes an avocado oil, a linseed oil, an almond oil, an insects wax, a perilla oil, an olive oil, a cocoa butter, a kapok wax, a kaya oil, a carnauba wax, a liver oil, a candelilla wax, a beef tallow, a neats-foot oil, a beef bone fat, a cured beef tallow, an apricot kernel oil, a whale wax, a hydrogenated oil, a wheat germ oil, a sesame oil, a rice germ oil, a rice bran oil, a sugarcane wax, a sasanqua oil, a safflower oil, a shea butter, a Chinese tung oil, a cinnamon oil, a jojoba wax, a shellac wax, a turtle oil, a soybean oil, a tea seed oil, a camellia oil, an evening primrose oil, a corn oil, a pig fat, a rapeseed oil, a Japanese tung oil, a bran wax, a germ oil, a horse fat, a persic oil, a palm oil, a palm kernel oil, a castor oil, a cured castor oil, a methyl ester of castor oil fatty acid, a sunflower oil, a grape seed oil, a bayberry wax, a jojoba oil, a macadamia nut oil, a bees wax, a mink oil, a cotton seed oil, a cotton wax, a Japan wax, a Japan wax kernel oil, a montan wax, a coconut oil, a cured coconut oil, a tri-coconut fatty acid glyceride, a mutton tallow, a peanut oil, lanolin, liquid lanolin, reduced lanolin, lanolin alcohol, hard lanolin, lanolin acetate, isopropyl lanolin fatty acid, POE lanolin alcohol ether, POE lanolin alcohol acetate, polyethylene glycol lanolin fatty acid, POE hydrogenated lanolin alcohol ether, and an egg-yolk oil.

Illustrative example of the hydrocarbon oil includes an ozocerite, squalane, squalene, a ceresin, a paraffin, a paraffin wax, a liquid paraffin, a pristane, polyisobutylene, a microcrystalline wax, and vaseline. Illustrative example of the higher fatty acid includes lauric acid, myristic acid, palmitic acid, stearic acid, behenic acid, undecylenic acid, oleic acid, linoleic acid, linolenic acid, arachidonic acid, eicosapentaenoic acid, docosahexaenoic acid, isostearic acid, and 12-hydroxystearic acid.

Illustrative example of the higher alcohol includes lauryl alcohol, myristyl alcohol, palmityl alcohol, stearyl alcohol, behenyl alcohol, hexadecyl alcohol, oleyl alcohol, isostearyl alcohol, hexyl dodecanol, octyl dodecanol, cetostearyl alcohol, 2-decyl tetradecynol, cholesterol, phytosterol, POE cholesterol ether, monostearyl glycerin ether (batyl alcohol), and monooleyl glycerine ether (selachyl alcohol).

Illustrative example of the ester oil includes diisobutyl adipate, 2-hexyldecyl adipate, di-2-heptylundecyl adipate, an N-alkylglycol monoisostearate, isocetyl isostearate, trimethylolpropane triisostearate, ethylene glycol di-2-ethylhexanoate, neopentyl glycol di-2-ethylhexanoate, cetyl 2-ethylhexanoate, trimethylolpropane tri-2-ethylhexanoate, pentaerythritol tetra-2-ethylhexanoate, cetyl octanoate, octyl dodecyl gum ester, oleyl oleate, octyldodecyl oleate, decyl oleate, neopentyl glycol dicaprate, triethyl citrate, 2-ethylhexyl succinate, amyl acetate, ethyl acetate, butyl acetate, isocetyl stearate, butyl stearate, diisopropyl sebacate, di-2-ethylhexyl sebacate, cetyl lactate, myristyl lactate, isopropyl palmitate, 2-ethylhexyl palmitate, 2-hexyldecyl palmitate, 2-heptylundecyl palmitate, cholesteryl 12-hydroxystearate, a dipentaerythritol fatty acid ester, isopropyl myristate, 2-octyldodecyl myristate, 2-hexyldecyl myristate, myristyl myristate, hexyldecyl dimethyloctanoate, ethyl laurate, hexyl laurate, 2-octyldodecyl N-lauroyl-L-glutamate ester, diisostearyl malate, dextrin palmitate ester, dextrin stearate ester, dextrin 2-ethylhexanoate palmitate ester, sucrose palmitate ester, sucrose stearate ester, monobenzylidene sorbitol, and dibenzylidene sorbitol.

Illustrative example of the glyceride oil includes acetoglyceryl, glyceryl diisooctanoate, glyceryl triisostearate, glyceryl triisopalmitate, glyceryl tri-2-ethylhexanoate, glyceryl monostearate, glyceryl di-2-heptylundecanoate, and glyceryl trimyristate.

Illustrative example of the silicone oil includes dimethyl polysiloxane, methyl phenyl polysiloxane, methyl hydrogen polysiloxane, octamethyl cyclotetrasiloxane, decamethyl cyclopentasiloxane, dodecamethyl cyclohexane siloxane, and tetramethyl tetrahydrogen cyclotetrasiloxane; a higher alkoxy-modfied silicone such as stearoxysilicone; a higher fatty acid-modified silicone; a fluorine-modified silicone; an amino-modified silicone; an alkyl-modified silicone; a silicone modified with a higher aliphatic acid ester; a silicone resin, a silicone rubber, and a silicone resin. Illustrative example of the fluorinated oil material includes a perfluoro polyether, perfluoro decalin, and perfluoro octane.

These oil materials may be used singly, or as a mixture of two or more of them, as necessarily. The cosmetic of the present invention may contain the foregoing oil with the amount thereof being 0 to 90.0% by mass, especially preferably 1 to 90% by mass. If the cosmetic of the present invention contains water as its ingredient, amount of water therein is 0 to 99.0% by mass.

Illustrative example of the alcohols usable in the present invention includes ethanol, propanol, ethylene glycol, ethylene glycol monoalkyl ether, diethylene glycol monoethyl ether, polyethylene glycol, propylene glycol, dipropylene glycol, 1,3-butylene glycol, glycerin, diglycerin, polyglycerin, pentaerythritol, sucrose, lactose, xylitol, sorbitol, mannitol, maltitol, carrageenan, agar, guar gum, dextrin, tragacanth gum, locust bean gum, polyvinyl alcohol, a polyoxyethylene-type polymer, a polyoxyethylene polyoxypropylene copolymer type polymer, hyaluronic acid, chondroitin sulfate, and chitin chitosan; these may be used singly, or as a mixture of two or more of them, as necessarily. Amount of these alcohols in the cosmetic is in the range of 0.1 to 90.0% by mass, or preferably 0.5 to 50.0% by mass. If the amount thereof is 0.1% or more by mass, sufficient moist property, antibacterial property, and antimold property may be obtained; while, if the amount thereof is 90.0% or less by mass, effect of powder composition of the present invention may be fully expressed; and thus, this range is desirable.

The cosmetic of the present invention is excellent by containing those ingredients mentioned above, but may further contain, in addition to the above, following ingredients i), ii), iii), and iv), if necessary.

i) Powders Shown Below (Including Colorant)

Illustrative example of the inorganic powder includes a powder of titanium oxide, zirconium oxide, zinc oxide, cerium oxide, magnesium oxide, barium sulfate, calcium sulfate, magnesium sulfate, calcium carbonate, magnesium carbonate, talc, mica, kaolin, sericite, white mica, synthetic mica, phlogopite, lepidolite, biotite, lithia mica, silicic acid, silicic acid anhydride, aluminum silicate, magnesium silicate, aluminum magnesium silicate, calcium silicate, barium silicate, strontium silicate, a metal tungstate salt, hydroxy apatite, vermiculite, higilite, bentonite, montomorillonite, hectorite, zeolite, ceramic powder, dicalcium phosphate, alumina, aluminum hydroxide, boron nitride, and silica.

Illustrative example of the organic powder includes polyamide powder, polyester powder, polyethylene powder, polypropylene powder, polystyrene powder, polyurethane powder, bezoguanamine powder, polymethyl benzoguanamine powder, tetrafluoroethylene powder, polymethyl methacrylate powder, cellulose powder, silk powder, nylon powder such as 12 nylon and 6 nylon, and other powders of styrene-acrylic acid copolymer, divinyl benzene, a styrene copolymer, a vinyl resin, an urea resin, a phenolic resin, a fluorinated resin, a silicone resin, an acryl resin, a melamine resin, an epoxy resin, a polycarbonate resin, fine crystalline fiber powder, a starch, and lauroyl lysine.

Illustrative example of the surfactant metal salt powder (metal soap) includes zinc stearate, aluminum stearate, calcium stearate, magnesium stearate, zinc myristate, magnesium myristate, zinc cetylphosphate, calcium cetylphosphate, and sodium cetylphosphate zinc.

Illustrative example of the color pigment includes an inorganic red pigment such as iron oxide, iron hydroxide, and iron titanate; an inorganic brown pigment such as γ-iron oxide; an inorganic yellow pigment such as yellow iron oxide and loess; an inorganic black pigment such as black iron oxide and carbon black; an inorganic purple pigment such as manganese violet and cobalt violet; an inorganic green pigment such as chromium hydroxide, chromium oxide, cobalt oxide, and cobalt titanate; an inorganic blue pigment such as Prussian blue and azurite; a laked tar dye; a laked natural dye; and a composite powder obtained by hybridization of these powders.

Illustrative example of the pearl pigment includes a mica coated with titanium oxide, oxychloro bismuth, oxychloro bismuth coated with titanium oxide, talc coated with titanium oxide, argentine, and color mica coated with titanium oxide; and illustrative example of the metal powder pigment includes aluminum powder, copper powder, and stainless powder.

Illustrative example of the tar dye includes Red No. 3, Red No. 104, Red No. 106, Red No. 201, Red No. 202, Red No. 204, Red No. 205, Red No. 220, Red No. 226, Red No. 227, Red No. 228, Red No. 230, Red No. 401, Red No. 505, Yellow No. 4, Yellow No. 5, Yellow No. 202, Yellow No. 203, Yellow No. 204, Yellow No. 401, Blue No. 1, Blue No. 2, Blue No. 201, Blue No. 404, Green No. 3, Green No. 201, Green No. 204, Green No. 205, Orange No. 201, Orange No. 203, Orange No. 204, Orange No. 206, and Orange No. 207; and illustrative example of the natural dye includes carminic acid, laccaic acid, carthamin, brazilin, and crocin.

These powders may be used independent of their forms (spherical, needle-like, plate-like, and so on), their particle diameters (fumed, microparticle, pigment-class, and so on), and their particle structures (porous, non-porous, and so on), as far as they are used in a usual cosmetic. Further, these powders may form a composite by hybridizing with each other, or may be treated their surfaces with an oil, a silicone other than the polyoxyalkylene-containing organopolysiloxane of the present invention or a fluorinated compound.

ii) Surfactants Shown Below

Illustrative example of the anionic surfactant includes a saturated or an unsaturated aliphatic acid soap such as sodium stearate and triethanolamine oleate, an alkyl ether carboxylic acid and a slat thereof, a carboxylate salt of a condensation product between an amino acid and a fatty acid or the like, an amide ether carboxylate salt, an α-sulfofatty acid ester salt, an α-acylsulfonate salt, an alkyl sulfonate salt, an alkene sulfonate salt, a sulfonate salt of a fatty acid ester, a sulfonate salt of a fatty acid amide, an alkyl sulfonate salt and a sulfonate salt of its formalin condensate, an alkyl sulfate ester salt, a sulfate ester salt of a secondary higher alcohol, a sulfate ester salt of an alkyl and an allyl ether, a sulfate ester salt of a fatty acid ester, a sulfate ester salt of a fatty acid alkylolamide, a sulfate ester salt of a Turkey red oil and so on, an alkyl phosphate salt, an alkenyl phosphate salt, an ether phosphate salt, an alkyl ally ether phosphate salt, an alkylamide phosphate salt, and an N-acylamino acid.

Illustrative example of the cationic surfactant includes an alkylamine salt, a salt of an amine such as polyamine and an aminoalcohol fatty acid derivative, an alkyl quaternary ammonium salt, an aromatic quaternary ammonium salt, a pyridinum salt, and an imidazolium salt.

Illustrative example of the nonionic surfactant includes a sorbitan fatty acid ester, a glycerin fatty acid ester, a polyglycerin fatty acid ester, a propylene glycol fatty acid ester, a polyethylene glycol fatty acid ester, a sucrose fatty acid ester, a polyoxyethylene alkyl ether, a polyoxypropylene alkyl ether, a polyoxyethylene alkyl phenyl ether, a polyoxyethylene fatty acid ester, a polyoxyethylene sorbitan fatty acid ester, a polyoxyethyelene sorbitol fatty acid ester, a polyoxyethylene glycerin fatty acid ester, a polyoxyethylene propylene glycol fatty acid ester, a polyoxyethylene castor oil, a polyoxyethylene hydrogenated castor oil, a polyoxyethylene phytostanol ether, a polyoxyethylene phytosterol ether, a polyoxyethylene cholestanol ether, a polyoxyethylene cholesteryl ether, a polyoxyalkylene-modified organopolysiloxane, an organopolysiloxane co-modified with a polyoxyalkylene and an alkyl, an organopolysiloxane co-modified with a polyoxyalkylene and a fluoroalkyl, a polyoxyalkylene-organopolysiloxane block copolymer, an alkanol amide, a sugar ether, and a sugar amide.

Illustrative example of the amphoteric surfactant includes a betaine, an aminocarboxylate, and an imidazoline derivative.

iii) Crosslinking Organopolysiloxane

In accordance with its purpose, the cosmetic of the present invention may contain one, or two or more of crosslinking organopolysiloxanes other than the organopolysiloxanes of the present invention. It is preferable that this crosslinking organopolysiloxane swell by absorbing the low viscous silicone having viscosity of 0.65 to 10.0 $mm^2$/second (25° C.) with the amount thereof being more than own weight of the crosslinking organopolysiloxane. In addition, it is preferable that this crosslinking organopolysiloxane have a crosslinking structure formed by reaction between a crosslinking agent having two or more reactive vinyl groups in its molecule and a hydrogen atom directly bonded to a silicon atom. Further, it is preferable that this crosslinking organopolysiloxane have at least one moiety selected from the group consisting of a polyoxyalkylene moiety, an alkyl moiety, an alkenyl moiety, an aryl moiety, and a fluoroalkyl moiety. If this crosslinking organopolysiloxane is used, amount thereof is preferably in the range of 0.1 to 30% by mass, in particular 1 to 10% by mass, relative to totality of the cosmetic.

iv) Silicone Resin Such as a Graft or a Block Acryl/Silicone Copolymer and a Silicone Net-Work Compound In accordance with its purpose, in the cosmetic of the present invention, at least one silicone resin selected from a graft or a block acryl/silicone copolymer, a silicone net-work compound, and the like may be used. In the present invention, an acryl silicone resin is especially preferable as this silicone resin. Further, it is preferable that this silicone resin be an acryl silicone resin which contains in its molecule at least one moiety selected from the group consisting of a pyrrolidone moiety, a long-chain alkyl moiety, a polyoxyalkylene moiety, and a fluoroalkyl moiety. In addition, it is preferable that this silicone resin be a net-work silicone compound. When a silicone resin such as the graft or block acryl/silicone copolymer and the net-work silicone compound is used, amount thereof to be blended is preferably 0.1 to 20% by mass, in particular 1 to 10% by mass, relative to totality of the cosmetic.

Specific preferable application of the cosmetic of the present invention includes a make-up product, a hair cosmetic, and a UV-cut product. Form of the product thereof is not particularly restricted; and it may be used as such states as a liquid, a milky emulsion, a cream, a solid, a paste, a gel, a powder, a multilayer, a mousse, and a spray.

As the most preferable application of the cosmetic of the present invention, a hair cosmetic may be mentioned. Amount of the organopolysiloxane of the present invention in the hair cosmetic is preferably 0.1 to 20% by mass (hereinafter, merely shown by %), more preferably 1 to 10%, or still more preferably 1 to 5% in view of obtaining good conditioning effect and its durability.

The hair cosmetic may be further blended with an oil, especially an oil having a conditioning effect to hairs. Illustrative example of the oil includes a lower alcohol; a saturated or an unsaturated alcohol having 12 to 30 carbon atoms; an ether of the foregoing alcohol with a polyalcohol; an ester of the foregoing alcohol with an aliphatic acid having 1 to 11 carbon atoms; a saturated or an unsaturated aliphatic acid having 12 to 30 carbon atoms; an ester of the foregoing aliphatic acid with a monovalent or a polyvalent alcohol; an amide of the foregoing aliphatic acid with an amine; a sterol; squalene; a phospholipid; a glycolipid; an animal fat and oil; a vegetable oil; and one or more silicones selected from a cyclic, a linear, or a branched dimethyl polysiloxane, methyl polysiloxane, polysiloxane, alkyl-modified silicone, methyl phenyl polysiloxane, and polyether-modified silicone.

Amount of these oil to be blended into the hair cosmetic is preferably 0.01 to 30%, more preferably 1 to 25%, or still more preferably 3 to 20%.

In addition, the hair cosmetic may be added as appropriate with a thickener such as hydroxyethyl cellulose, a surfactant, an anionic, an amphoteric, a cationic, or a nonionic polymer, a fragrance, a material to afford a pearl-like appearance, a hair-setting polymer, a color pigment, an UV absorber, an antioxidant, and a preservative.

There is no particular restriction as to the surfactant, provided that it is used in a usual hair cosmetic; and thus, any of an anionic, a nonionic, an amphoteric, and a cationic surfactant may be used suitably.

Illustrative example of the anionic surfactant to be blended to the hair cosmetic includes the followings: an alkylbenzene sulfonate salt, preferably a linear or a branched alkylbenzene sulfonate salt having an alkyl group having average 10 to 16 carbon atoms; an alkyl ether sulfate salt or an alkenyl ether sulfate salt, preferably an alkyl ether sulfate salt or an alkenyl ether sulfate salt having a linear or a branched alkyl or an alkenyl group having average 10 to 20 carbon atoms, wherein the alkyl ether sulfate salt or the alkenyl ether sulfate salt is an adduct of ethylene oxide, propylene oxide, or butylene oxide with the average number thereof in one molecule being 0.5 to 8 mole and with molar ratio of ethylene oxide to propylene oxide being 0.1/9.9 to 9.9/0.1 or ethylene oxide to butylene oxide being 0.1/9.9 to 9.9/0.1; an alkylsulfate salt or an alkenylsulfate salt, preferably an alkylsulfate salt or an alkenylsulfate salt having an alkyl group or an alkenyl group having average 10 to 20 carbon atoms; an olefin sulfonate salt, preferably an olefin sulfonate salt having average 10 to 20 carbon atoms in one molecule; an alkane sulfonate salt, preferably an alkane sulfonate salt having average 10 to 20 carbon atoms in one molecule; a higher fatty acid salt, preferably a saturated or an unsaturated fatty acid salt having average 10 to 24 carbon atoms in one molecule; a surfactant of an (amide)ether carboxylic acid type; an α-sulfo fatty acid salt or ester, preferably an α-sulfo fatty acid salt or an ester having an alkyl group or an alkenyl group having average 10 to 20 carbon atoms; a surfactant of an N-acyl aminoacid type, preferably a surfactant of an N-acyl aminoacid type having a free carboxylic acid residue and an acyl group having 8 to 24 carbon atoms (for example, N-acyl sarcosinate and N-acyl-β-alanine); a surfactant of a phosphate ester type, preferably a surfactant of a phosphate mono- or di-ester type having an alkyl group or an alkenyl group having 8 to 24 carbon atoms, or an alkylene oxide adduct thereof; a surfactant of a sulfosuccinate ester type, preferably a surfactant of a sulfosuccinate ester of a higher alcohol having 8 to 22 carbon atoms or an ethoxylate thereof or a sulfosuccinate ester derived from a higher aliphatic acid amide; a polyoxyalkylene fatty acid amide ether sulfate salt, preferably a sulfate salt of an ethoxylate and so forth of a linear or a branched, a saturated or an unsaturated, aliphatic acid monoethanol amide or diethanol amid having 8 to 24 carbon atoms; a monoglyceride sulfate ester salt; a monoglyceride sulfate ester salt, preferably a monoglyceride sulfate ester salt having a linear or a branched, a saturated or an unsaturated, aliphatic acid group having 8 to 24 carbon atoms; an acylated isethionate salt, preferably an acylated isethionate salt having a linear or a branched, a saturated or an unsaturated, aliphatic acid group having 8 to 24 carbon atoms; an alkyl glyceryl ether sulfate salt or an alkyl glyceryl ether sulfonate salt, preferably an alkyl glyceryl ether sulfate salt or an alkyl glyceryl ether sulfonate salt having a linear or a branched alkyl group, alkenyl group, or alkylene oxide adduct of them having 8 to 24 carbon atoms; an alkyl or an alkenyl amide sulfonate, preferably an alkyl or an alkenyl amide sulfonate having a linear or a branched alkyl or alkenyl group having 8 to 24 carbon atoms; an alkanol amide sulfosuccinate salt, preferably an alkanol amide sulfosuccinate salt having a linear or a branched alkyl or alkenyl group having 8 to 24 carbon atoms; an alkyl sulfoacetate, preferably an alkyl sulfoacetate having a linear or a branched alkyl or alkenyl group having 8 to 24 carbon atoms; an acylated taurate, preferably an acylated taurate having a linear or a branched, a saturated or an unsaturated, aliphatic acid group having 8 to 24 carbon atoms; and an N-acyl-N-carboxyethyl glycine salt, preferably an N-acyl-N-carboxyethyl glycine salt having an acyl group having 6 to 24 carbon atoms.

Illustrative example of the counter ion of these anionic surfactant salt, namely the counter ion of an anionic residue thereof includes an alkaline metal ion such as sodium and potassium; an alkaline earth metal ion such as calcium and magnesium; ammonium ion; and an alkanol amine having 1 to 3 alkanol groups having 2 or 3 carbon atoms (for example, monoethanol amine, diethanol amine, triethanol amine, and triisopropanol amine).

Among these anionic surfactants, an alkyl ether sulfate salt, in particular, a polyoxyethylene alkyl ether sulfate salt is preferable.

Illustrative example of the nonionic surfactant to be blended in the hair cosmetic includes a polyoxyalkylene alkyl ether or a polyoxyalkylene alkenyl ether having a linear or a branched alkyl or alkenyl group having average 10 to 24 carbon atoms and being an adduct of ethylene oxide, propylene oxide, or butylene oxide; a glycerin ester of a fatty acid having 8 to 20 carbon atoms; a glycol ester of a fatty acid having 8 to 20 carbon atoms; an alkylene oxide adduct of monoglyceride of a fatty acid having 8 to 20 carbon atoms; a sucrose ester of a fatty acid having 8 to 20 carbon atoms; a sorbitan ester of a fatty acid having 8 to 20 carbon atoms; a polyglycerin fatty acid ester having an acyl group having 8 to 20 carbon atoms; a monoethanol amide, diethanol amide, or their ethoxylate of a fatty acid having 8 to 20 carbon atoms; a polyoxyethylene cured castor oil; a polyoxyalkylene sorbitan fatty acid ester having an acyl group having 8 to 20 carbon atoms; a polyoxyethylene sorbit fatty acid ester having an acyl group having 8 to 20 carbon atoms; an alkyl saccharide-type surfactant having a linear or a branched alkyl, an alkenyl or an alkyl phenyl group having 8 to 18 carbon atoms; an alkylamine oxide or an alkylamide amine oxide having a linear or a branched alkyl group, or an alkenyl group having 8 to 20 carbon atoms; an ether compound or an ester compound of a polyalcohol having a linear or a branched alkyl or an alkenyl group having 8 to 20 carbon atoms; an organopolysiloxane modified with polyoxyalkylene; an organopolysiloxane co-modified with polyoxyalkylene and an alkyl; an organopolysiloxane modified with polyglycerin; an organopolysiloxane co-modified with polyglycerin and an alkyl; an organopolysiloxane co-modified with a polyoxyalkylene and a fluoroalkyl; a crosslinking polyoxyalkylene organopolysiloxane; a sugar-modified silicone; an oxazoline-modified silicone; a polyoxyalkylene alkyl aryl ether; a polyoxyalkylene lanolin alcohol; a polyoxyalkylene fatty acid ester; a pluronic block polymer; a tetronic block polymer; a polyoxyalkylene fatty acid amide; a polyoxyalkylene alkylamide; and a polyethylene imine derivative.

As to the amphoteric surfactant, there is no particular restriction, provided that it is used in a usual hair cosmetic; and illustrative example thereof includes an amide amino type, a carbobetaine type, an amide betaine type, a sulfobetaine type, an amide sulfobetaine type, an imidazolinium betaine type, an aminoacid type, a phosphobetaine type, and a phosphate ester type.

As to the cationic surfactant, a tertiary amine, a quaternary ammonium salt, an amide amine, an ester amine, and so forth may be mentioned. Illustrative example thereof includes behenyl trimethyl ammonium chloride, distearyl dimethyl ammonium chloride, cetyl trimethyl ammonium chloride, stearyl trimethyl ammonium chloride, lauryl trimethyl ammonium chloride, N-stearyl-N,N,N-tri(polyoxyethylene) ammonium chloride (addition of total 3 mol ethylene oxides), cetyl benzyl dimethyl ammonium chloride, cetyl triethyl ammonium bromide, distearyl dimethyl ammonium chloride, 2-decyltetradecyl trimethyl ammonium chloride, 2-dodecyl-hexadecyl trimethyl ammonium chloride, di-2-hexyldecyl dimethyl ammonium chloride, di-2-octyldodecyl dimethyl ammonium chloride, behenyl tertiary amine, stearyl tertiary amine, and stearamidepropyl dimethyl amine.

These surfactants may be used singly or as a mixture of two or more of them; and in order to have a good foaming property, amount thereof in the hair cosmetic is preferably 0.1 to 50%, more preferably 0.5 to 40%, and in particular 1 to 30%.

When the hair cosmetic is in a form of hair setting, hair foaming, hair spray, and so forth, it is preferable to contain following exemplified polymers as a hair setting polymer therein: polyvinyl pyrrolidone; copolymer of polyvinyl pyrrolidone and vinyl acetate; crosslinked copolymer of polyvinyl pyrrolidone, vinyl acetate, and vinyl propionic acid; copolymer of polyvinyl pyrrolidone and an alkyl aminoacrylate; copolymer of polyvinyl pyrrolidone, an acrylate, and (meth)acrylic acid; copolymer of polyvinyl pyrrolidone, an alkyl aminoacrylate, and vinyl caprolactam; copolymer of methyl vinyl ether and a maleic anhydride alkyl half ester; copolymer of vinyl acetate and crotonic acid; copolymer of vinyl acetate, crotonic acid, and vinyl neodecanoic acid, copolymer of vinyl acetate, crotonic acid, and vinyl propionic acid, copolymer of vinyl acetate, vinyl tert-butylbenzoic acid, and crotonic acid;

copolymer of (meth)acrylic acid and a (meth)acrylate ester, copolymer of acrylic acid, an alkly acrylate ester, and an alkyl acrylamide; copolymer of (meth)acryl ethyl betaine and an alkyl (meth)acrylate ester; copolymer of N-methacryloyloxy-ethyl-N,N-dimethyl ammonium α-N-methylcarboxy betaine and an alkyl (meth)acrylate ester: copolymer of an alkyl acrylate ester, butylaminoethyl methacrylate, and acrylic acid octylamide;

a basic acryl polymer;

a compound having a cellulose skeleton and a cationic cellulose derivative;

a salt of hydroxypropyl chitosan, carboxymethyl chitin, carboxymethyl chitosan, and chitosan with a monovalent acid such as pyrrolidone carboxylic acid, lactic acid, and glycol acid or with a divalent acid such as adipic acid and succinic acid; and a water-dispersible polyester.

These hair setting polymers may be used singly or as a mixture of two or more of them. Amount of the hair setting polymer in the hair cosmetic is preferably 0.1 to 10%, more preferably 0.5 to 6%, or in particular 1 to 4%, to obtain a sufficient and necessary setting power.

Illustrative example of the hair cosmetic includes materials used in a home place and a beauty salon; and thus, those used in a bath room, such as a hair shampoo, a hair treatment, and a hair conditioner; those used outside a bath room, such as a hair foam, a hair spray, a hair cream, a hair wax, and a hair gel; and in addition, a hair dye, a hair permanent, a hair manicure, and a hair bleach. The organopolysiloxane compound of the present invention may be blended to any of them.

Powder Dispersion in Oil

In addition, the present invention provides a powder dispersion in oil obtained by dispersing powders, which are treated with a powder dispersant, into an oil material.

The powder dispersion in oil may be obtained by dispersing powders, which are treated with a powder treating material, into an oil material; or alternatively after a powder treating material is dissolved or dispersed in an oil material, powders may be added thereinto and mixed for dispersion. In any of these cases, the form thereof is a liquid dispersion. This powder dispersion in oil may be prepared arbitrarily by, for example, following heretofore known methods.

1. Method wherein powders which are treated with a powder treating material are added into an oil material such as an ester oil and a silicone oil and then they are mixed for dispersion.
2. Method wherein a powder treating material is dissolved or dispersed into the oil material mentioned above, and then this is mixed with powders by using a dispersing equipment such as a ball mill and a sand mill.

The powder dispersion in oil thus obtained may be blended and used as it is.

The powders may be any of an inorganic powder, an organic powder, a surfactant metal salt powder (metal soap), a color pigment, a pearl pigment, a metal powder pigment, a tar dye, and a natural dye.

Illustrative example of the inorganic powder includes a powder of titanium oxide, zirconium oxide, zinc oxide, cerium oxide, magnesium oxide, barium sulfate, calcium sulfate, magnesium sulfate, calcium carbonate, magnesium carbonate, talc, mica, kaolin, sericite, white mica, synthetic mica, phlogopite, lepidolite, biotite, lithia mica, silicic acid, silicic acid anhydride, aluminum silicate, magnesium silicate, aluminum magnesium silicate, calcium silicate, barium silicate, strontium silicate, a metal tungstate salt, hydroxy apatite, vermiculite, higilite, bentonite, montomorillonite, hectorite, zeolite, ceramic powder, dibasic calcium phosphate, alumina, aluminum hydroxide, boron nitride, and silica. For the cosmetic use, extender pigments such as mica and sericite, zinc oxide, titanium oxide, and so on are preferable.

Illustrative example of the organic powder includes polyamide powder, polyester powder, polyethylene powder, polypropylene powder, polystyrene powder, polyurethane powder, benzoguanamine powder, polymethyl benzoguanamine powder, tetrafluoroethylene powder, polymethyl methacrylate powder, cellulose powder, silk powder, nylon powder such as 12 nylon and 6 nylon, and other powders of styrene-acrylic acid copolymer, divinyl benzene-styrene copolymer, a vinyl resin, an urea resin, a phenolic resin, a fluorinated resin, a silicone resin, an acryl resin, a melamine resin, an epoxy resin, a polycarbonate resin, fine crystalline fiber powder, a starch, and lauroyl lysine.

Illustrative example of the surfactant metal salt powder (metal soap) includes zinc stearate, aluminum stearate, calcium stearate, magnesium stearate, zinc myristate, magnesium myristate, zinc cetylphosphate, calcium cetylphosphate, and sodium cetylphosphate zinc.

Illustrative example of the color pigment includes an inorganic red pigment such as iron oxide, iron hydroxide, and iron titanate; an inorganic brown pigment such as γ-iron oxide; an inorganic yellow pigment such as yellow iron oxide and loess; an inorganic black pigment such as black iron oxide and carbon black; an inorganic purple pigment such as manganese violet and cobalt violet; an inorganic green pigment such as chromium hydroxide, chromium oxide, cobalt oxide, and cobalt titanate; an inorganic blue pigment such as Prussian blue and azurite; a laked tar dye; a laked natural dye; and a composite powder obtained by hybridization of these powders.

Illustrative example of the pearl pigment includes a mica coated with titanium oxide, oxychloro bismuth, oxychloro bismuth coated with titanium oxide, talc coated with titanium oxide, fish scale foil, and color mica coated with titanium oxide; and illustrative example of the metal powder pigment includes aluminum powder, copper powder, and stainless powder.

Illustrative example of the tar dye includes Red No. 3, Red No. 104, Red No. 106, Red No. 201, Red No. 202, Red No. 204, Red No. 205, Red No. 220, Red No. 226, Red No. 227, Red No. 228, Red No. 230, Red No. 401, Red No. 505, Yellow No. 4, Yellow No. 5, Yellow No. 202, Yellow No. 203, Yellow No. 204, Yellow No. 401, Blue No. 1, Blue No. 2, Blue No. 201, Blue No. 404, Green No. 3, Green No. 201, Green No. 204, Green No. 205, Orange No. 201, Orange No. 203, Orange No. 204, Orange No. 206, and Orange No. 207; and illustrative example of the natural dye includes carminic acid, laccaic acid, carthamin, brazilin, and crocin.

These powders may be used independent of their forms (spherical, needle-like, plate-like, and so on), their particle diameters (fumed, microparticle, pigment-class, and so on), and their particle structures (porous, non-porous, and so on). Further, these powders may form a composite by themselves, or may be treated their surfaces with an oil material, a silicone, or a fluorinated compound.

Illustrative example of the silicone oil includes dimethyl polysiloxane, methyl phenyl polysiloxane, octamethyl cyclotetrasiloxane (D4), decamethyl cyclopentasiloxane (D5), dodecamethyl cyclohexasiloxane (D6), decamethyl tetrasiloxane (M3T), a silicone modified with a higher alkoxy such as stearoxysilicone, a higher fatty acid-modified silicone, a fluorine-modified silicone, an amino-modified silicone, an alkyl-modified silicone, and a silicone modified with a higher aliphatic acid ester; illustrative example of the fluorinated oil material includes perfluoro polyether, perfluoro decalin, and perfluoro octane; illustrative example of the glyceride oil includes acetoglyceryl, glyceryl diisooctanoate, glyceryl triisostearate, glyceryl triisopalmitate, glyceryl tri-2-ethylhexanoate, glyceryl monostearate, glyceryl di-2-heptylundecanoate, and glyceryl trimyristate; illustrative example of the ester oil includes diisobutyl adipate, 2-hexyldecyl adipate, di-2-heptylundecyl adipate, an N-alkylglycol monoisostearate, isocetyl isostearate, trimethylolpropane triisostearate, ethylene glycol di-2-ethylhexanoate, neopentyl glycol di-2-ethylhexanoate, cetyl 2-ethylhexanoate, trimethylolpropane tri-2-ethylhexanoate, pentaerythritol tetra-2-ethylhexanoate, cetyl octanoate, octyl dodecyl gum ester, oleyl oleate, octyldodecyl oleate, decyl oleate, neopentyl glycol dicaprate, triethyl citrate, 2-ethylhexyl succinate, amyl acetate, ethyl acetate, butyl acetate, isocetyl stearate, butyl stearate, diisopropyl sebacate, di-2-ethylhexyl sebacate, cetyl lactate, myristyl lactate, isopropyl palmitate, 2-ethylhexyl palmitate, 2-hexyldecyl palmitate, 2-heptylundecyl palmitate, cholesteryl 12-hydroxystearate, a dipentaerythritol fatty acid ester, isopropyl myristate, 2-octyldodecyl myristate, 2-hexyldecyl myristate, myristyl myristate, hexyldecyl dimethyloctanoate, ethyl laurate, hexyl laurate, 2-octyldodecyl N-lauroyl-L-glutamate ester, diisostearyl malate, dextrin palmitate ester, dextrin stearate ester, dextrin 2-ethylhexanoate palmitate ester, sucrose palmitate ester, sucrose stearate ester, monobenzylidene sorbitol, and dibenzylidene sorbitol; illustrative example of the hydrocarbon oil includes an ozocerite, squalane, squalene, a ceresin, a paraffin, a liquid paraffin, a pristane, and polyisobutylene; illustrative example of the alcohol includes ethanol, propanol, ethylene glycol, ethylene glycol monoalkyl ether, diethylene glycol monoethyl ether, polyethylene glycol, propylene glycol, dipropylene glycol, 1,3-butylene glycol, glycerin, diglycerin, and polyglycerin; illustrative example of the natural vegetable and animal fatty oil and the semi-synthetic oil includes an avocado oil, a linseed oil, an almond oil, an insects wax, a perilla oil, an olive oil, a cocoa butter, a kapok wax, a kaya oil, a carnauba wax, a liver oil, a candelilla wax, a beef tallow, a neats-foot oil, a beef bone fat, a cured beef tallow, an apricot kernel oil, a whale wax, a hydrogenated oil, a wheat germ oil, a sesame oil, a rice germ oil, a rice bran oil, a sugarcane wax, a sasanqua oil, a safflower oil, a shea butter, a Chinese tung oil, a cinnamon oil, a jojoba wax, a shellac wax, a turtle oil, a soybean oil, a tea seed oil, a camellia oil, an evening primrose oil, a corn oil, a pig fat, a rapeseed oil, a Japanese tung oil, a bran wax, a germ oil, a horse fat, a persic oil, a palm oil, a palm kernel oil, a castor oil, a cured castor oil, a methyl ester of cured castor oil fatty acid, a sunflower oil, a grape seed oil, a bayberry wax, a jojoba oil, a macadamia nut oil, a bees wax, a mink oil, a cotton seed oil, a cotton wax, a Japan wax, a Japan wax kernel oil, a montan wax, a coconut oil, a cured coconut oil, a tri-coconut fatty acid glyceride, a mutton tallow, a peanut oil, lanolin, liquid lanolin, reduced lanolin, lanolin alcohol, hard lanolin, lanolin acetate, isopropyl lanolin fatty acid, POE lanolin alcohol ether, POE lanolin alcohol acetate, polyethylene glycol lanolin fatty acid, POE hydrogenated lanolin alcohol ether, and an egg-yolk oil. Meanwhile, POE means polyoxyethylene.

Use amount of the dispersant is 0.1 to 30 parts by mass, or preferably 0.5 to 10 parts by mass, relative to 100 parts by mass of the powders. The dispersion bodies as mentioned above may be added as a filler to a personal care composition, especially to a cosmetic composition and various compositions such as a thermoplastic or a thermosetting composition and a rubber composition.

EXAMPLES

Hereinafter, the present invention will be specifically explained by showing Examples and Comparative Examples; but the present invention is not limited to the following Examples. Meanwhile, amount of each component in the Tables is based on pure amount thereof unless otherwise noted. The kinematic viscosity is a measured value at 25° C. by using an Oswald viscometer.

Example 1

Into a reactor were taken 100 parts by mass of organohydrogen polysiloxane having kinematic viscosity of 53 mm²/second (25° C.) and shown by the following average composition formula,

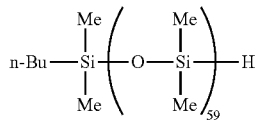

30 parts by mass of 2-propanol, 6.8 parts by mass of the polyoxyalkylene compound having 3.28 mmol/g of the vinyl value and shown by the below-shown formula, and 0.02 parts by mass of a 1-butanol solution of chloroplatinic acid (3% by weight of platinum); and then, they were stirred at 80° C. for 4 hours. A part of the reaction mixture was withdrawn and measured with FT-IR (Fourier Transform Infrared Spectrometer; manufactured by Thermo Fisher Scientific K. K.) and ¹HNMR (CDC13, 400 MHz, manufactured by Bruker Corp.); and after it was confirmed that the peaks derived from the Si—H had been disappeared, the reaction was terminated,

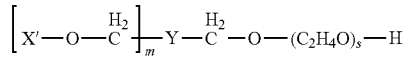

wherein X' is $CH_2$=CH—$CH_2$—; Y is the below-shown formula; s=9 and m=2.

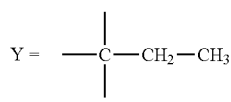

The reaction mixture thus obtained was stripped under reduced pressure at 120° C. to remove the solvent to obtain a colorless and transparent liquid of the polyoxyalkylene-modified organopolysiloxane having the kinematic viscosity of 270 mm²/second (25° C.)

Example 2

Into a reactor were taken 100 parts by mass of organohydrogen polysiloxane having kinematic viscosity of 53 mm²/second (25° C.) and shown by the following average composition formula,

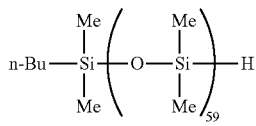

30 parts by mass of tetrahydrofuran, 5.3 parts by mass of the polyoxyalkylene compound having 4.44 mmol/g of the vinyl value and shown by the below-shown formula, and 0.02 parts by mass of a 1-butanol solution of chloroplatinic acid (3% by weight of platinum); and then, they were stirred at 70° C. for 5 hours. A part of the reaction mixture was withdrawn and measured with FT-IR (Fourier Transform Infrared Spectrometer; manufactured by Thermo Fisher Scientific K. K.) and ¹HNMR (CDCl₃, 400 MHz, manufactured by Bruker Corp.); and after it was confirmed that the peaks derived from the Si—H had been disappeared, the reaction was terminated,

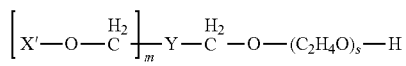

wherein X' is $CH_2$=CH—$CH_2$—; Y is the below-shown formula (carbon atom); s=9 and m=3.

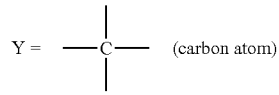

The reaction mixture thus obtained was stripped under reduced pressure at 110° C. to remove the solvent to obtain a pale yellowish, slightly turbid liquid of the polyoxyalkylene-modified organopolysiloxane having the kinematic viscosity of 170 mm²/second (25° C.)

Example 3

Into a reactor were taken 200 parts by mass of organohydrogen polysiloxane having kinematic viscosity of 5.4 mm²/second (25° C.) and shown by the following average composition formula,

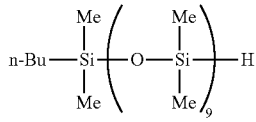

50 parts by mass of toluene, 56 parts by mass of the polyoxyalkylene compound having 4.44 mmol/g of the vinyl value and shown by the below-shown formula, and 0.03 parts by mass of a 1-butanol solution of chloroplatinic acid (3% by weight of platinum); and then, they were stirred at 100° C. for 4 hours. A part of the reaction mixture was withdrawn and measured with FT-IR (Fourier Transform Infrared Spectrometer; manufactured by Thermo Fisher Scientific K. K.) and ¹HNMR (CDCl₃, 400 MHz, manufactured by Bruker Corp.); and after it was confirmed that the peaks derived from the Si—H had been disappeared, the reaction was terminated,

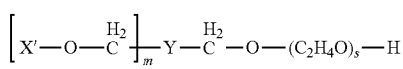

wherein X' is $CH_2=CH-CH_2-$; Y is the below-shown formula (carbon atom); s=9 and m=3.

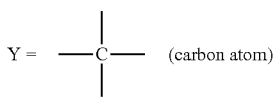

The reaction mixture thus obtained was stripped under reduced pressure at 130° C. to remove the solvent to obtain a pale yellowish solid (20° C.) of the polyoxyalkylene-modified organopolysiloxane.

Example 4

Into a reactor were taken 300 parts by mass of organohydrogen polysiloxane having kinematic viscosity of 270 mm²/second (25° C.) and shown by the following average composition formula,

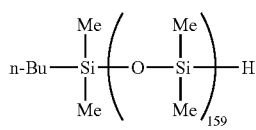

100 parts by mass of 2-propanol, 26 parts by mass of the polyoxyalkylene compound having 0.971 mmol/g of the vinyl value and shown by the below-shown formula, and 0.03 parts by mass of a 1-butanol solution of chloroplatinic acid (3% by weight of platinum); and then, they were stirred at 85° C. for 7 hours. A part of the reaction mixture was withdrawn and measured with FT-IR (Fourier Transform Infrared Spectrometer; manufactured by Thermo Fisher Scientific K. K.) and ¹HNMR (CDCl₃, 400 MHz, manufactured by Bruker Corp.); and after it was confirmed that the peaks derived from the Si—H had been disappeared, the reaction was terminated,

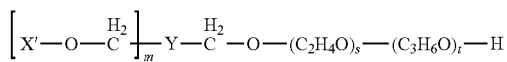

wherein X' is $CH_2=CH-CH_2-$; Y is the below-shown formula; s=18, t=18, and m=2.

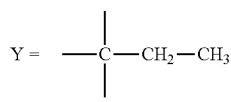

The reaction mixture thus obtained was stripped under reduced pressure at 110° C. to remove the solvent to obtain a pale yellowish, slightly turbid liquid of the polyoxyalkylene-modified organopolysiloxane having the kinematic viscosity of 1010 mm²/second (25° C.)

Example 5

Into a reactor were taken 500 parts by mass of organohydrogen polysiloxane having kinematic viscosity of 24 mm²/second (25° C.) and shown by the following average composition formula,

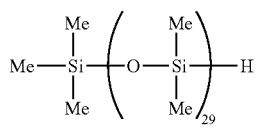

150 parts by mass of 2-propanol, 84 parts by mass of the polyoxyalkylene compound having 2.61 mmol/g of the vinyl value and shown by the below-shown formula, and 0.06 parts by mass of a 1-butanol solution of chloroplatinic acid (3% by weight of platinum); and then, they were stirred at 85° C. for 5 hours. A part of the reaction mixture was withdrawn and measured with FT-IR (Fourier Transform Infrared Spectrometer; manufactured by Thermo Fisher Scientific K. K.) and ¹HNMR (CDCl₃, 400 MHz, manufactured by Bruker Corp.); and after it was confirmed that the peaks derived from the Si—H had been disappeared, the reaction was terminated,

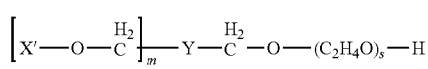

wherein X' is $CH_2=C(CH_3)-CH_2-$; Y is the below-shown formula (carbon atom); s=18 and m=3.

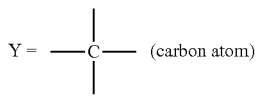

The reaction mixture thus obtained was stripped under reduced pressure at 110° C. to remove the solvent to obtain a pale yellowish solid (20° C.) of the polyoxyalkylene-modified organopolysiloxane.

Example 6

Into a reactor were taken 100 parts by mass of organohydrogen polysiloxane having kinematic viscosity of 5.4 mm²/second (25° C.) and shown by the following average composition formula,

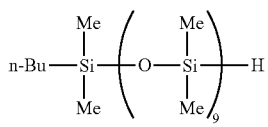

20 parts by mass of 2-propanol, 25 parts by mass of the polyoxyalkylene compound having 5.12 mmol/g of the vinyl value and shown by the below-shown formula, and 0.01 parts by mass of a 1-butanol solution of chloroplatinic acid (3% by weight of platinum); and then, they were stirred at 80° C. for 4 hours. A part of the reaction mixture was withdrawn and measured with FT-IR (Fourier Transform Infrared Spectrometer; manufactured by Thermo Fisher Scientific K. K.) and $^1$HNMR (CDCl$_3$, 400 MHz, manufactured by Bruker Corp.); and after it was confirmed that the peaks derived from the Si—H had been disappeared, the reaction was terminated,

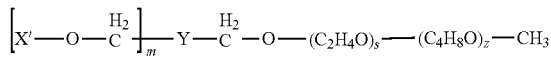

wherein X' is CH$_2$=CH—CH$_2$—; Y is the below-shown formula; s=2, z=1, and m=2.

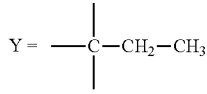

The reaction mixture thus obtained was stripped under reduced pressure at 120° C. to remove the solvent to obtain a colorless and transparent liquid of the polyoxyalkylene-modified organopolysiloxane having the kinematic viscosity of 60 mm$^2$/second (25° C.)

Comparative Example 1

Into a reactor were taken 100 parts by mass of organohydrogen polysiloxane having kinematic viscosity of 53 mm$^2$/second (25° C.) and shown by the following average composition formula,

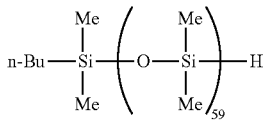

30 parts by mass of 2-propanol, 10.3 parts by mass of the polyoxyalkylene compound having 2.15 mmol/g of the vinyl value and shown by the below-shown formula, and 0.01 parts by mass of a 1-butanol solution of chloroplatinic acid (3% by weight of platinum); and then, they were stirred at 85° C. for 5 hours. A part of the reaction mixture was withdrawn and measured with FT-IR (Fourier Transform Infrared Spectrometer; manufactured by Thermo Fisher Scientific K. K.) and $^1$HNMR (CDCl$_3$, 400 MHz, manufactured by Bruker Corp.); and after it was confirmed that the peaks derived from the Si—H had been disappeared, the reaction was terminated.

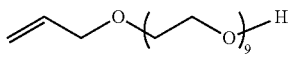

The reaction mixture thus obtained was stripped under reduced pressure at 110° C. to remove the solvent to obtain a pale yellowish, slightly turbid liquid of the polyoxyalkylene-modified organopolysiloxane having the kinematic viscosity of 570 mm$^2$/second (25° C.)

Comparative Example 2

Into a reactor were taken 200 parts by mass of organohydrogen polysiloxane having kinematic viscosity of 5.4 mm$^2$/second (25° C.) and shown by the following average composition formula,

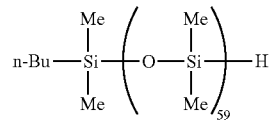

50 parts by mass of toluene, 64 parts by mass of the polyoxyalkylene compound having 3.92 mmol/g of the vinyl value and shown by the below-shown formula, and 0.02 parts by mass of a 1-butanol solution of chloroplatinic acid (3% by weight of platinum); and then, they were stirred at 85° C. for 5 hours. A part of the reaction mixture was withdrawn and measured with FT-IR (Fourier Transform Infrared Spectrometer; manufactured by Thermo Fisher Scientific K. K.) and $^1$HNMR (CDCl$_3$, 400 MHz, manufactured by Bruker Corp.); and after it was confirmed that the peaks derived from the Si—H had been disappeared, the reaction was terminated.

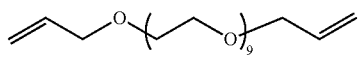

The reaction mixture thus obtained was stripped under reduced pressure at 110° C. to remove the solvent to obtain a colorless and transparent liquid of the polyoxyalkylene-modified organopolysiloxane having the kinematic viscosity of 80 mm$^2$/second (25° C.)

Examples 7 to 9 and Comparative Examples 3 to 5

By using the reaction products obtained by Examples 1 to 3 and Comparative Examples 1 to 2, creams of the present invention and for comparison, having the compositions (% by mass) shown in Table 1, were prepared by a usual method (Examples 7 to 9 and Comparative Examples 3 to 5).

The creams thus obtained were evaluated according to the following method. The results thereof are shown in Table 1.

Evaluation Method:

Emulsion stabilities of the creams shown in Table 1 were evaluated by visual observation after one month and three months at 50° C.

Evaluation criteria are as following:

Excellent: No separation

Good: Slight separation in the upper layer

Fair: Separation in the upper layer

Poor: Separation into the upper and the lower layers.

A cream which was obtained after preparation was applied on a skin with the amount thereof being 2 g; and after it was fully familiarized with a skin, evaluation thereof was carried out. Sensory evaluation were performed as to absence of stickiness, extendability, and lightless at the time of application. Evaluation criteria are as shown below based on number of the panelists who replied with the answer, "Yes, it is effective".

Evaluation Criteria:

Excellent: 4 to 5 panelists replied with Yes.

Good: 3 panelists replied with Yes.

Fair: 2 panelists replied with Yes.

TABLE 1

| | | Examples | | | Comparative Examples | | |
|---|---|---|---|---|---|---|---|
| | | 7 | 8 | 9 | 3 | 4 | 5 |
| 1 | Polyoxyalkylene-modified organopolysoloxane of Example 1 | 2 | | | | | |
| 2 | Polyoxyalkylene-modified organopolysoloxane of Example 2 | | 2 | | | | |
| 3 | Polyoxyalkylene-modified organopolysoloxane of Example 3 | | | 2 | | | |
| 4 | Polyoxyalkylene-modified organopolysoloxane of Comparative Example 1 | | | | 2 | | |
| 5 | Polyoxyalkylene-modified organopolysoloxane of Comparative Example 2 | | | | | 2 | |
| 6 | KF-6017 *1 | | | | | | 2 |
| 7 | Decamethyl cyclopenta-siloxane | 4 | 4 | 4 | 4 | 4 | 4 |
| 8 | Dimethyl polysiloxane (6 mm²/s) | 6 | 6 | 6 | 6 | 6 | 6 |
| 9 | Squalane | 2 | 2 | 2 | 2 | 2 | 2 |
| 10 | Mineral oil | 1 | 1 | 1 | 1 | 1 | 1 |
| 11 | KSG-15 *2 | 9 | 9 | 9 | 9 | 9 | 9 |
| 12 | KSG-210 *3 | 1 | 1 | 1 | 1 | 1 | 1 |
| 13 | 1,3-Butlyene glycol | 6 | 6 | 6 | 6 | 6 | 6 |
| 14 | Sodium citrate | 0.2 | 0.2 | 0.2 | 0.2 | 0.2 | 0.2 |
| 15 | Sodium chloride | 0.2 | 0.2 | 0.2 | 0.2 | 0.2 | 0.2 |
| 16 | Ethanol | 4 | 4 | 4 | 4 | 4 | 4 |
| 17 | Purified water | Remainder | Remainder | Remainder | Remainder | Remainder | Remainder |
| Evaluation | Emulsion stability after one month at 50° C. | Excellent | Excellent | Excellent | Good | Good | Good |
| | Emulsion stability after three months at 50° C. | Excellent | Excellent | Excellent | Fair | Fair | Good |
| | Non-stickiness | Excellent | Good | Excellent | Good | Fair | Poor |
| | Extendability | Good | Good | Excellent | Fair | Good | Fair |
| | Lightness at the time of application | Good | Good | Excellent | Fair | Fair | Fair |

*1 KF-6017: Polyether-modified silicone (manufactured by Shin-Etsu Chemical Co., Ltd.)
*2 KSG-15: Dimethyl polysiloxane elastomer (manufactured by Shin-Etsu Chemical Co., Ltd.)
*3 KSG-210: Polyether-modified dimethyl polysiloxane elastomer (manufactured by Shin-Etsu Chemical Co., Ltd.)

From the results shown in Table 1, creams of Examples 7 to 9 gave a cosmetic having higher temporal stability of emulsion, lower stickiness, better extendability, and lighter feeling as compared with creams of Comparative Examples 3 to 5.

Examples 10 to 12 and Comparative Examples 6 to 8

The following water-in-oil liquid foundations were prepared by a usual method.

The obtained liquid foundations were evaluated according to the following method. The results thereof are shown in Table 2.

Evaluation Method:

Emulsion stabilities of the liquid foundations shown in Table 2 were evaluated by visual observation after three months at 50° C.

Evaluation criteria are as following:
Excellent: No separation
Good: Slight separation in the upper layer
Fair: Separation in the upper layer
Poor: Separation into the upper and the lower layers.

The liquid foundation which was obtained after preparation was applied on a skin with the amount thereof being 2 g; and after it was fully familiarized with a skin, evaluation thereof was carried out. Sensory evaluation were performed as to uniformity of color tone, absence of stickiness, cosmetic durability, and lightness at the time of application. Evaluation criteria are as shown below based on number of the panelists who replied with the answer, "Yes, it is effective".

Evaluation Criteria:
Excellent: 4 to 5 panelists replied with Yes.
Good: 3 panelists replied with Yes.
Fair: 2 panelists replied with Yes.
Poor: 1 or zero panelist replied with Yes.

TABLE 2

|   |   | Examples | | | Comparative Examples | | |
|---|---|---|---|---|---|---|---|
|   |   | 10 | 11 | 12 | 6 | 7 | 8 |
| 1 | Polyoxyalkylene-modified organopolysoloxane of Example 1 | 2 | | | | | |
| 2 | Polyoxyalkylene-modified organopolysoloxane of Example 2 | | 2 | | | | |
| 3 | Polyoxyalkylene-modified organopolysoloxane of Example 3 | | | 2 | | | |
| 4 | Polyoxyalkylene-modified organopolysoloxane of Comparative Example 1 | | | | 2 | | |
| 5 | Polyoxyalkylene-modified organopolysoloxane of Comparative Example 2 | | | | | 2 | |
| 6 | KF-6017 *1 | | | | | | 2 |
| 7 | Decamethyl cyclopentasiloxane | 45 | 45 | 45 | 45 | 45 | 45 |
| 8 | Dimethyl polysiloxane (6 mm$^2$/s) | 5 | 5 | 5 | 5 | 5 | 5 |
| 9 | Montomorillonite modified by octadecyl dimethyl benzyl ammonium salt | 4 | 4 | 4 | 4 | 4 | 4 |
| 10 | Hydrophobized titanium oxide *2 | 10 | 10 | 10 | 10 | 10 | 10 |
| 11 | Hydrophobized talc *2 | 6 | 6 | 6 | 6 | 6 | 6 |
| 12 | Hydrophobized mica *2 | 6 | 6 | 6 | 6 | 6 | 6 |
| 13 | Hydrophobized red iron oxide *2 | 1.5 | 1.5 | 1.5 | 1.5 | 1.5 | 1.5 |
| 14 | Hydrophobized black iron oxide *2 | 0.7 | 0.7 | 0.7 | 0.7 | 0.7 | 0.7 |
| 15 | Hydrophobized yellow iron oxide *2 | 0.2 | 0.2 | 0.2 | 0.2 | 0.2 | 0.2 |
| 16 | Dipropylene glycol | 5 | 5 | 5 | 5 | 5 | 5 |
| 17 | Sodium citrate | 0.2 | 0.2 | 0.2 | 0.2 | 0.2 | 0.2 |
| 18 | Fragrance | 0.1 | 0.1 | 0.1 | 0.1 | 0.1 | 0.1 |
| 19 | Purified water | Remainder | Remainder | Remainder | Remainder | Remainder | Remainder |
| Evaluation | Emulsion stability after three months at 50° C. | Excellent | Excellent | Good | Fair | Fair | Good |
|   | Uniformity of color tone | Excellent | Excellent | Good | Fair | Fair | Good |
|   | Non-stickiness | Excellent | Good | Excellent | Fair | Good | Poor |
|   | Cosmetic durability | Excellent | Good | Excellent | Poor | Good | Fair |
|   | Lightness at the time of application | Good | Good | Excellent | Fair | Fair | Poor |

*1 KF-6017: Polyether-modified silicone (manufactured by Shin-Etsu Chemical Co., Ltd.)
*2 Hydrophobization treatment: After methyl hydrogen polysiloxane was added to the powders with the amount thereof relative to the powders being 2%, the resulting mixture was subject to the heat treatment.

From the results shown in Table 2, the liquid foundations of Examples 10 to 12 gave a cosmetic having higher temporal stability of emulsion, better dispersion stability of the powders with uniform color tone, no stickiness, better cosmetic durability, and lighter feeling as compared with the liquid foundations of Comparative Examples 6 to 8.

Example 13

Hair Treatment

A hair treatment having the composition as shown below was prepared by a usual method.

| Composition | Mass (%) |
|---|---|
| Octadecyloxy(2-hydroxypropyl)dimethylamine | 0.5 |
| Stearic acid dimethylaminopropylamide | 2.0 |
| Stearyl alcohol | 5.0 |
| Dipropylene glycol | 1.0 |
| Benzyl alcohol | 0.5 |
| Phenoxy ethanol | 0.1 |
| Polyoxyalkylene-modified organopolysiloxane of Example 4 | 2.5 |
| Highly polymerized dimethyl polysiloxane* | 0.5 |
| Glycerin | 5.0 |
| Polypropylene glycol | 2.5 |
| Lanolin fatty acid | 0.5 |

-continued

| Composition | Mass (%) |
|---|---|
| Sunflower oil | 0.5 |
| Lactic acid | 1.5 |
| Fragrance | 0.4 |
| Sodium hydroxide | 0.1 |
| Ion-exchanged water | remainder |

*KF-96H 100000 cs (Manufactured by Shin-Etsu Chemical Co., Ltd.)

The hair treatment thus obtained did not change with passage of time while being moisture, non-sticky, smooth, soft, and excellent in combing.

Example 14

Lip Stick

A lip stick having the composition as shown below was prepared by a usual method.

| (Ingredients) | Mass (%) |
|---|---|
| Candelilla wax | 8.0 |
| Polyethylene wax | 8.0 |
| Long chain alkyl-containing acryl silicone resin (*1) | 12.0 |
| Methyl phenyl polysiloxane (*2) | 3.0 |
| Isotridecyl isononanoate | 20.0 |
| Glyceryl isostearate | 16.0 |
| Polyoxyalkylene-modified organopolysiloxane of Example 1 | 0.5 |
| Montomorillonite modified by octadecyl dimethyl benzyl ammonium salt | 0.5 |
| Polyglyceryl triisostearate | 27.3 |
| Silicone-treated Red No. 202 (*3) | 0.8 |
| Silicone-treated red iron oxide (*3) | 1.5 |
| Silicone-treated yellow iron oxide (*3) | 1.0 |
| Silicone-treated black iron oxide (*3) | 0.2 |
| Silicone-treated titanium oxide (*3) | 1.0 |
| Preservative | 0.1 |
| Fragrance | 0.1 |

(*1) Long chain alkyl-containing acryl silicone resin: KP-561P (trade name: manufactured by Shin-Etsu Chemical Co., Ltd.)
(*2) Methyl phenyl polysiloxane: KF-54 (trade name: manufactured by Shin-Etsu Chemical Co., Ltd.)
(*3) Treated with acryl silicone-based graft copolymer: KP-541 (trade name: manufactured by Shin-Etsu Chemical Co., Ltd.)

The lip stick thus obtained had shiny surface with light spreading property and without oiliness and powderiness while giving fresh use feeling. In addition, it was excellent in water resistance, water repellency, cosmetic durability, and stability.

Example 15

Eye Liner

An eye liner having the composition as shown below was prepared by a usual method.

| (Ingredients) Composition | Mass (%) |
|---|---|
| Decamethyl cyclopentasiloxane | 22.0 |
| Dimethyl polysiloxane (6 mm²/second) | 5.0 |
| Black iron oxide | 20.0 |
| Vitamin E acetate | 0.2 |
| Jojoba oil | 2.0 |
| Bentonite | 3.0 |
| Polyoxyalkylene-modified organopolysiloxane of Example 6 | 2.0 |

-continued

| (Ingredients) Composition | Mass (%) |
|---|---|
| Ethanol | 10.0 |
| 1,3-Butylene glycol | 10.0 |
| Preservative | 0.1 |
| Fragrance | 0.1 |
| Purified water | remainder |

It was confirmed that the eye liner thus obtained has a light spreading property and thus is easy to draw; and in addition, it has a clean and fresh use feeling without stickiness. There was no change by temperature or passage of time; and in addition, it was excellent not only in usability, stability, water-resistance, and perspiration resistance but also in cosmetic durability.

Example 16

Milky Lotion

A milky lotion having the composition as shown below was prepared by a usual method.

| (Ingredients) | Mass (%) |
|---|---|
| Decamethyl cyclopentasiloxane | 15.0 |
| Methyl phenyl polysiloxane | 5.0 |
| Squalene | 5.0 |
| Pentaerythritol tetra-2-ethylhexanoate | 5.0 |
| Polyoxyalkylene-modified organopolysiloxane of Example 2 | 3.0 |
| Organopolysiloxane elastomer spherical powder (*1) | 2.0 |
| Hydrophobic silica (*2) | 0.5 |
| Magnesium ascorbate phosphate | 1.0 |
| Sodium chloride | 1.0 |
| Polyethylene glycol 11000 | 1.0 |
| Propylene glycol | 8.0 |
| Preservative | 0.1 |
| Fragrance | 0.1 |
| Purified water | remainder |

(*1) Organopolysiloxane elastomer spherical powder: KMP-590 (manufactured by Shin-Etsu Chemical Co., Ltd.)
(*2) Hydrophobic silica: Aerosil R972 (manufactured by Nippon Aerosil Co., Ltd.)

It was found that the milky lotion thus obtained has wide and light spreading properties, and a fresh and non-sticky use feeling. There was no change by temperature or passage of time; and in addition, it was excellent in usability and stability.

Example 17

O/W Cream

An o/w cream having the composition as shown below was prepared by a usual method.

| (Ingredients) | Mass (%) |
|---|---|
| Crosslinking dimethyl polysiloxane (*1) | 8.0 |
| Crosslinking methyl phenyl polysiloxane (*2) | 2.0 |
| Isotridecyl isononanoate | 5.0 |
| Dipropylene glycol | 7.0 |
| Glycerin | 5.0 |
| Methyl cellulose (2% aqueous solution) (*3) | 7.0 |
| Polyacrylamide emulsifier (*4) | 2.0 |
| Polyoxyalkylene-modified organopolysiloxane of Example 5 | 0.5 |

-continued

| (Ingredients) | Mass (%) |
| --- | --- |
| Guanine | 1.0 |
| Preservative | 0.1 |
| Fragrance | 0.1 |
| Purified water | Remainder |

(*1) Crosslinking dimethyl polysiloxane: KSG-16 (manufactured by Shin-Etsu Chemical Co., Ltd.)
(*2) Crosslinking methyl phenyl polysiloxane: KSG-18 (manufactured by Shin-Etsu Chemical Co., Ltd.)
(*3) Methyl cellulose: Metolose SM-4000 (manufactured by Shin-Etsu Chemical Co., Ltd.)
(*4) Polyacrylamide emulsifier: Sepigel 305 (manufactured by SEPIC S. A.)

The cream thus obtained gave an o/w cream having wide and light spreading properties and moistening and refreshing use feeling with fineness and without stickiness and greasiness; and in addition, it has good cosmetic durability and stability with no change by temperature or passage of time.

Example 18

Powder Foundation

A powder foundation having the composition as shown below was prepared by a usual method.

| (Ingredients) | Mass (%) |
| --- | --- |
| Vaseline | 2.5 |
| Squalane | 3.0 |
| Polyoxyalkylene-modified organopolysiloxane of Example 3 | 0.5 |
| Glyceryl trioctanoate | 2.0 |
| Silicone-treated mica (*1) | 40.0 |
| Silicone-treated talc (*1) | 22.2 |
| Silicone-treated titanium oxide (*1) | 10.0 |
| Silicone-treated titanium oxide microparticles (*1) | 5.0 |
| Silicone-treated barium sulfate (*1) | 10.0 |
| Pigment | 0.1 |
| Phenyl-modified hybrid silicone composite powder (*2) | 2.0 |
| Silicone powder (*3) | 2.5 |
| Preservative | 0.1 |
| Fragrance | 0.1 |

(*1) Treated with acryl silicone-based graft copolymer: KP-541 (manufactured by Shin-Etsu Chemical Co., Ltd.)
(*2) Phenyl-modified hybrid silicone composite powder: KSP-300 (manufactured by Shin-Etsu Chemical Co., Ltd.)
(*3) Silicone powder: KMP-590 (manufactured by Shin-Etsu Chemical Co., Ltd.)

The powder foundation thus obtained showed excellent adhesion and a light and wide spreading property without stickiness; and in addition, it has excellent cosmetic durability with shiny finishing.

It must be noted here that the present invention is not limited to the embodiments as described above. The foregoing embodiments are mere examples; any form having substantially the same composition as the technical concept described in claims of the present invention and showing similar effects is included in the technical scope of the present invention.

What is claimed is:

1. An organopolysiloxane shown by the following average composition formula (1),

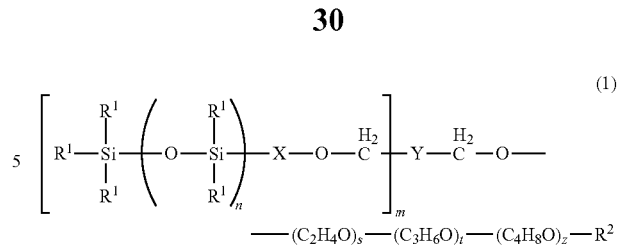

wherein each $R^1$ independently represents a monovalent hydrocarbon group having 1 to 12 carbon atoms; $R^2$ represents any of a hydrogen atom, a monovalent hydrocarbon group having 1 to 15 carbon atoms, and a monovalent acyl group having 1 to 6 carbon atoms; "n" represents an integer of 0 to 1000; "m" represents 2 or 3; X represents a divalent hydrocarbon group having 2 to 15 carbon atoms; Y represents C—$CH_2$—$CH_3$ when "m" represents 2 or Y represents a carbon atom when "m" represents 3; "s" represents an integer of 0 to 100; "t" represents an integer of 0 to 50; "z" represents an integer of 0 to 50, and wherein s+t+z is from 1 to 100.

2. A cosmetic wherein the organopolysiloxane according to claim 1 is contained therein.

3. A method for preparing the organopolysiloxane of claim 1, wherein a compound shown by the following average composition formula (2) and a compound shown by the following general formula (3) are reacted in the presence of a transition metal catalyst,

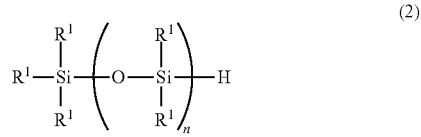

wherein each $R^1$ independently represents a monovalent hydrocarbon group having 1 to 12 carbon atoms; "n" represents an integer of 0 to 1000,

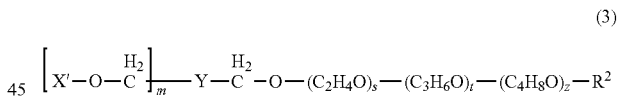

wherein X' represents a divalent hydrocarbon group having a C=C double bond at a terminal and has 2 to 15 carbon atoms; "m" represents 2 or 3; Y represents C—$CH_2$—$CH_3$ when "m" represents 2 of Y represents a carbon atom when "m" represents 3; $R^2$ represents any of a hydrogen atom, a monovalent hydrocarbon group having 1 to 15 carbon atoms, and a monovalent acyl group having 1 to 6 carbon atoms; "s" represents an integer of 0 to 100; "t" represents an integer of 0 to 50; "z" represents an integer of 0 to 50, and wherein s+t+z is from 1 to 100.

4. The method for preparing of an organopolysiloxane according to claim 3, wherein the transition metal catalyst contains at least one element of platinum and rhodium.

* * * * *